(12) United States Patent
Chan

(10) Patent No.: US 7,118,549 B2
(45) Date of Patent: Oct. 10, 2006

(54) SHUNT SYSTEM INCLUDING A FLOW CONTROL DEVICE FOR CONTROLLING THE FLOW OF CEREBROSPINAL FLUID OUT OF A BRAIN VENTRICLE

(75) Inventor: Ian Chan, San Francisco, CA (US)

(73) Assignee: Codman & Shurtleff, Inc., Raynham, MA (US)

( * ) Notice: Subject to any disclaimer, the term of this patent is extended or adjusted under 35 U.S.C. 154(b) by 293 days.

(21) Appl. No.: 10/699,273

(22) Filed: Oct. 31, 2003

(65) Prior Publication Data

US 2005/0096581 A1    May 5, 2005

(51) Int. Cl.
*A61M 5/00* (2006.01)
*F16K 31/08* (2006.01)

(52) U.S. Cl. .............. 604/10; 604/9; 251/65
(58) Field of Classification Search .............. 604/7–10, 604/264, 403, 411, 415, 416, 533–535, 905; 251/129.01, 315.01, 129.14, 205–208, 65; 137/217, 409, 433, 449, 430, 436, 247.13, 137/247.21, 15.22, 15.26, 215, 533.1; 206/363–366, 206/219; 222/129; 215/DIG. 8
See application file for complete search history.

(56) References Cited

U.S. PATENT DOCUMENTS

| | | | |
|---|---|---|---|
| 609,062 A | 8/1898 | Webb | |
| 2,753,990 A | 7/1956 | Chalfin et al. | |
| 3,166,083 A * | 1/1965 | Girden | 137/388 |
| 3,206,160 A * | 9/1965 | Bennett | 251/65 |
| 3,373,498 A * | 3/1968 | Chabbert | 33/364 |
| 3,883,113 A * | 5/1975 | Kolb | 251/209 |
| 3,889,687 A | 6/1975 | Harris et al. | |
| 3,897,809 A | 8/1975 | Steinberg | |
| 4,289,165 A * | 9/1981 | Fredd | 137/625.32 |
| 4,298,038 A | 11/1981 | Jennings | |
| 4,443,214 A | 4/1984 | Marion | |
| 4,552,553 A | 11/1985 | Schulte et al. | |
| 4,560,375 A | 12/1985 | Schulte et al. | |
| 4,610,658 A | 9/1986 | Buchwald et al. | |
| 4,615,691 A * | 10/1986 | Hakim et al. | 604/9 |
| 4,636,194 A | 1/1987 | Schulte et al. | |
| 4,651,904 A | 3/1987 | Schuckmann | |
| 4,673,384 A | 6/1987 | Marion | |
| 4,795,437 A | 1/1989 | Schulte et al. | |
| 5,165,576 A | 11/1992 | Hickerson | |
| 5,167,615 A | 12/1992 | East et al. | |
| 5,176,627 A | 1/1993 | Watson | |
| 5,185,809 A | 2/1993 | Kennedy et al. | |
| 5,342,025 A * | 8/1994 | Hwang | 251/65 |

(Continued)

Primary Examiner—Patricia Bianco
Assistant Examiner—Leslie R. Deak

(57) ABSTRACT

An anti-siphon device limits the flow of a fluid from a first region of a patient's body to a second region. The device includes a housing having a spherical inner surface with a predetermined inner diameter. The housing has an inlet port for receiving fluid from the first region and an outlet port for directing fluid to the second region. The inlet port and the outlet port are disposed approximately diametrically opposite from each other. A spherical ball is disposed within the housing. The spherical ball has a ferromagnetic weight disposed off center therein. The spherical ball has an outer diameter that is less than the inner diameter of the housing so that the spherical ball is free to rotate within the housing and the fluid is free to flow between the inner surface of the housing and an outer surface of said spherical ball. The spherical ball has a circumferential recess extending through its center.

30 Claims, 3 Drawing Sheets

U.S. PATENT DOCUMENTS

| | | |
|---|---|---|
| 5,556,011 A | 9/1996 | Jennings et al. |
| 5,643,194 A | 7/1997 | Negre |
| 5,692,945 A | 12/1997 | Crowell et al. |
| 5,695,093 A | 12/1997 | Lucius |
| 5,773,414 A | 6/1998 | Cody et al. |
| 5,884,816 A | 3/1999 | Hinze |
| 5,894,856 A * | 4/1999 | Swenson et al. .............. 137/38 |
| 6,007,814 A | 12/1999 | Scheinberg |
| 6,126,628 A | 10/2000 | Nissels |
| 6,383,160 B1 | 5/2002 | Madsen |

* cited by examiner

SHUNT SYSTEM INCLUDING A FLOW CONTROL DEVICE FOR CONTROLLING THE FLOW OF CEREBROSPINAL FLUID OUT OF A BRAIN VENTRICLE

BACKGROUND OF THE INVENTION

1. Field of the Invention

The present invention relates to a surgically implantable physiological shunt system and an anti-siphon device. More specifically, the present invention relates to a shunt system including a flow control device for controlling the flow of cerebrospinal fluid out of a brain ventricle.

2. Discussion of the Related Art

Shunt systems for directing body fluid from one region to another are known in the medical field. One application for such a fluid shunt system is in the treatment of hydrocephalus in order to direct cerebrospinal fluid away from the brain and into the venous system or to another region of the body. In this application, a shunt is implanted on the patient's skull, under the scalp, and is coupled to a brain ventricle catheter, which is adapted for insertion into the brain, and to a distal catheter, which is adapted for insertion into the drainage region, such as the peritoneal cavity, the atrium or other drainage site.

Generally, fluid shunt systems include a valve mechanism for controlling, or regulating the fluid flow rate. Illustrative valve mechanisms operate to permit fluid flow only once the fluid pressure reaches a certain level and may permit adjustment of the pressure level at which fluid flow commences.

One such adjustable valve, described in U.S. Pat. No. 4,551,128 (Hakim et al.), includes a flexible diaphragm and plate positioned to divide a housing into inlet and outlet chambers which communicate through an aperture in the plate. A valve element is biased against the aperture to close the aperture until the fluid pressure in the inlet chamber exceeds a preselected "popping pressure." The popping pressure is adjustable by adjusting an external screw of the valve. However, due to the elastomeric properties of the diaphragm material, maintenance of the implanted valve may be required. Further, flow rate adjustment of the Hakim et al. device after implantation may require a surgical procedure.

Another adjustable valve mechanism, described in U.S. Pat. No. 4,781,673 (Watanabe), includes two parallel fluid flow passages, with each passage including a flow rate regulator and an on-off valve. Fluid flow through the passages is manually controlled by palpably actuating the on-off valves through the scalp. Although the Watanabe device permits flow rate control palpably through the scalp and thus, without surgical intervention, patient and/or physician attention to the valve settings is required.

Effective fluid flow rate control is particularly important since overdrainage of cerebrospinal fluid can result in dangerous conditions, including subdural hematoma. Overdrainage tends to occur when a patient moves from a horizontal position to a sitting or standing position, due to a siphon effect in the shunt system. In order to reduce the risk of overdrainage, some shunt systems include additional devices, sometimes referred to as anti-siphon devices, for preventing overdrainage. Some such devices use weights, which move in response to the patient changing position, to open or close the fluid flow path. One system, described in U.S. Pat. No. 5,368,556 (Lecuyer), includes spherical weights which provide additional compressive force against a valve spring to help maintain the valve in a closed position when the patient is sitting or standing. However, noise associated with the use of such multiple weights may be objectionable.

SUMMARY OF THE INVENTION

An anti-siphon device for limiting the flow of a fluid from a first region of a patient's body to a second region in accordance with the present invention overcomes these deficiencies in the related art by providing a housing having a spherical inner surface with a predetermined inner diameter. The housing has an inlet port for receiving fluid from the first region and an outlet port for directing fluid to the second region. The inlet port and the outlet port are disposed approximately diametrically opposite from each other. A spherical ball is disposed within the housing. The spherical ball has a ferromagnetic weight disposed off center therein. The spherical ball has an outer diameter that is less than the inner diameter of the housing so that the spherical ball is free to rotate within the housing and the fluid is free to flow between the inner surface of the housing and an outer surface of said spherical ball. The spherical ball has a recess extending about the circumference of the ball.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein.

DETAILED DESCRIPTION OF THE PRESENTLY PREFERRED EXEMPLARY EMBODIMENT

Figure 1:
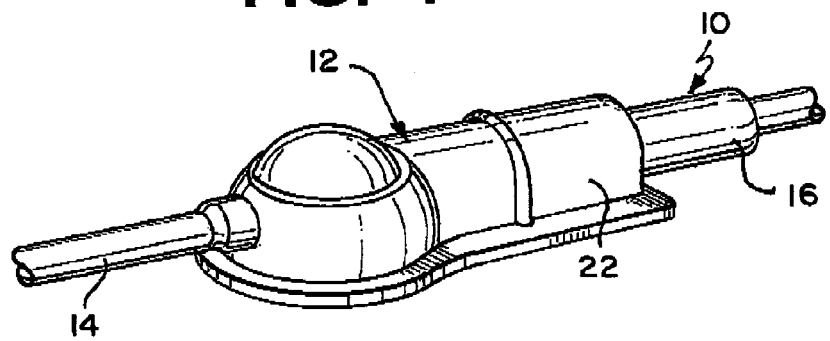
FIG. 1 is a perspective view of a shunt system incorporating a device for limiting the flow of a fluid from a first region of a patient's body to a second region in accordance with the present invention.

Referring now to FIGS. 1–4, a system 10 for limiting the flow of a fluid from a first region of a patient's body to a second region is illustrated. The system includes a housing 12 having an inlet 14 and an outlet 16. A one-way valve 18 is disposed within housing 12. The spring bias of the one-way valve is preferably programmable, as is taught in U.S. Pat. Nos. 4,615,691 and 4,772,257 to Hakim et al. and U.S. Pat. No. 5,928,182 to Kraus et al., the disclosures of which are hereby incorporated by reference in their entirety.

A subhousing 22 is disposed within housing 20, downstream from one-way valve 18. Subhousing 22 has a spherical inner surface 24 with a predetermined inner diameter. The subhousing 22 has an inlet port 26 for receiving fluid from the first region and an outlet port 28 for directing fluid to the second region. The inlet port 26 and the outlet port 28 are disposed approximately diametrically opposite from each other along essentially the same longitudinal axis A—A, as shown in FIG. 3.

Figure 2:
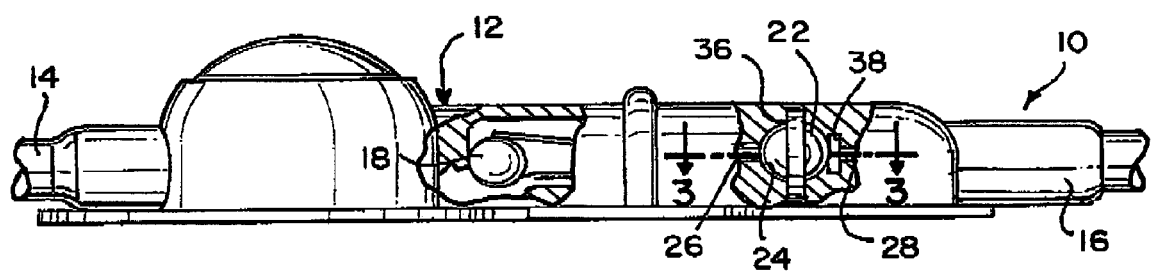
FIG. 2 is a side view of the shunt system of FIG. 1 with parts broken away.

A spherical ball 30 is disposed within subhousing 22. Spherical ball 30 has a ferromagnetic weight 32 disposed off center therein. The remainder of spherical ball may be made of a light-weight material, such as, for example, a biocompatible plastic. Plastic is preferred because it is light weight and has a smooth surface. In addition, spherical ball 30, with the exception of weight 32, may be hollow to create a maximum weight difference in ball 30. Ball 30 has a predetermined outer diameter that is less than the inner diameter of the subhousing 22. The ratio of the inner diameter of the subhousing 22 to the outer diameter of the ball is preferably around 1.25:1. Also, preferably, the cross-sectional area of the device is slightly smaller than the shunt so as to fit within the shunt housing, as illustrated in FIG. 2. Thus, the spherical ball 30 is free to rotate within subhousing 22 and the fluid is free to flow between the inner surface of the subhousing and an outer surface of the spherical ball. Spherical ball 30 has a recess 34 extending about the circumference of the ball.

Figure 3:
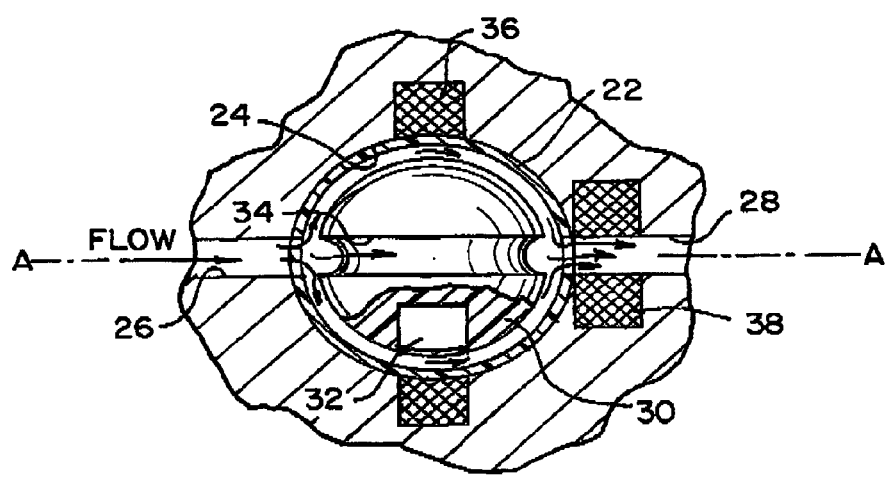
FIG. 3 is a cross-sectional view taken along lines 3—3 of FIG. 2 and looking in the direction of the arrows.
Figure 4:
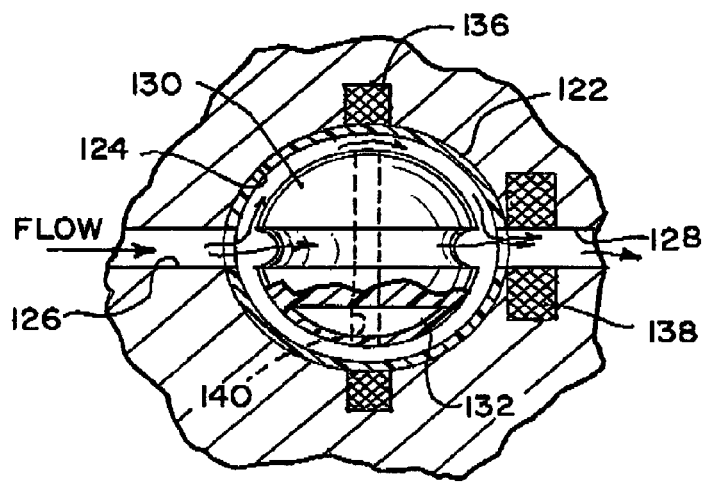
FIG. 4 is a cross-sectional view, similar to FIG. 3, but showing the device in another position.

Referring now to FIGS. 3 and 4, a first magnetic band 36 surrounds subhousing 22. The first magnetic band 36 has a plane of symmetry that is approximately normal to a line extending between the inlet port 26 and said outlet port 28. A second magnetic band 38 is disposed about outlet port 28. The second magnetic band 38 also has a plane of symmetry that is approximately normal to the line extending between the inlet port 26 and said outlet port 28. The first magnetic band 36 has one charge and the magnetic weight 32 has an opposite charge so that, in one position as illustrated in FIG. 2, they are magnetically attracted toward one another. The second magnetic band 38 has the same charge as the first magnetic band so that, in a second position illustrated in FIG. 3, second magnetic band 38 and magnetic weight 32 are magnetically attracted toward one another.

Subhousing 22 is preferably made of a material that reduces electromagnetic interference. Subhousing 22 is preferably made of metal, such as aluminum or titanium.

In use, when the patient is in the supine position (e.g., lying down), subhousing 22 is placed essentially in a first position which causes the magnetic weight in the spherical ball to align with the first magnetic band such that the circumferential recess 34 within ball 30 is approximately co-linear with respect to the line between the inlet port 26 and the outlet port 28. Thus, the maximum amount of fluid can flow through subhousing 22.

When the patient is in the upright position (e.g. standing or sitting up), subhousing 22 is placed essentially in a second position which causes the magnetic weight in the spherical ball to align with the second magnetic band 38 such that the circumferential recess 34 within ball 30 is normal with respect to the line between the inlet port 26 and the outlet port 28. The first position is disposed approximately ninety degrees from the second position.

The use of magnetic bands 36, 38 is not required, but is preferred to ensure that ball 30 will be aligned as illustrated in FIGS. 2 and 3 even when the patient is not disposed in a position that is exactly horizontal or vertical, respectively. For example, should a patient rest his/her head on a pillow, the patient's head may not be exactly horizontal, but may be inclined at an angle of, for example, 20 degrees. When the patient's head is inclined, the magnetic attraction between the magnetic weight 32 within ball 30 and band 36 will cause recess 34 to align with the inlet and outlet ports 26, 28. However, if the patient were to sit or stand up the angle of inclination will continue to increase until the magnetic weight 32 in ball 30 will be forced by gravity to move to the second position where weight 32 is aligned with second band 36 and recess 34 is at a right angle with respect to the line between the inlet port 26 and the outlet port 28. Thus, no fluid will effectively pass through recess 34 and the only path from inlet port 26 to outlet port 28 will be between the outer surface of ball 30 and the inner surface of subhousing 22.

Figure 5:
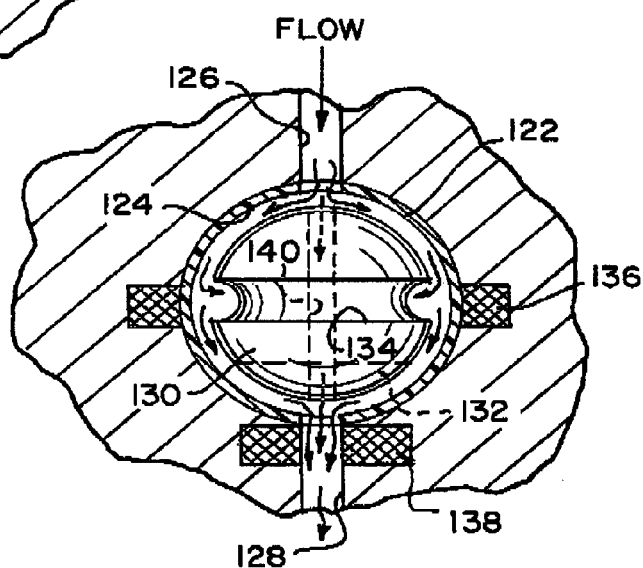
FIG. 5 is a cross-sectional view, similar to FIG. 3, but showing the device without the magnetic bands and in another position.

If magnetic bands 36, 38 are not used, as illustrated in FIG. 5, weight 32 will always be drawn by the force of gravity to the lowest possible position within subhousing 22. Thus, as the patient moves from the supine position to the vertical position, the recess 34 will move gradually between the two extreme positions. Thus, the flow rate through the anti-siphon device will gradually reduce from the maximum flow rate (as shown if FIG. 2) to the minimum flow rate (as shown in FIG. 3).

Figure 6:
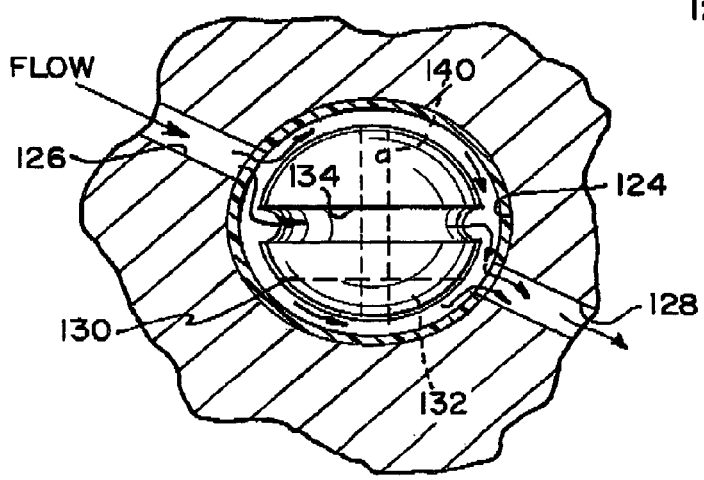
FIG. 6 is a cross-sectional view of another embodiment of the device in accordance with the present invention, shown with the device in a supine position.
Figure 7:
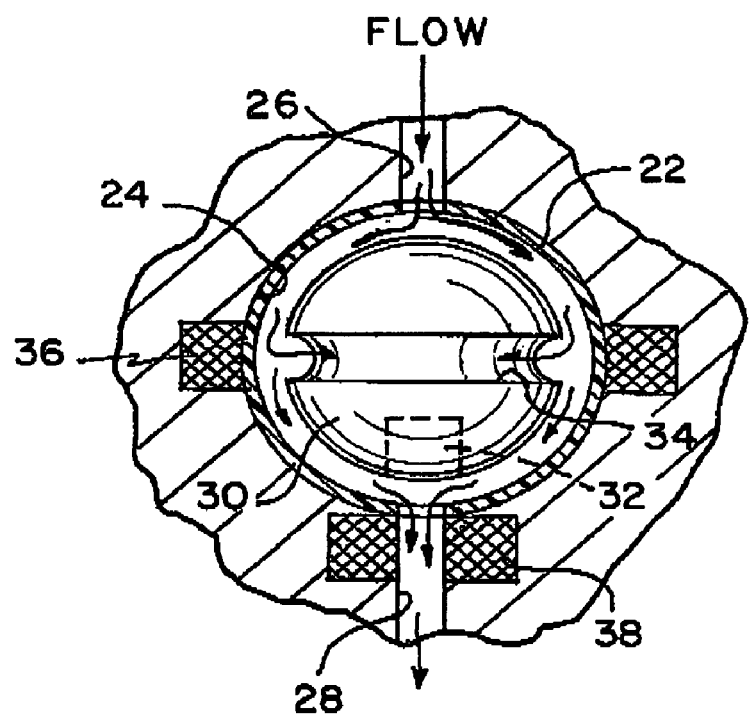
FIG. 7 is a cross-sectional view of the device of FIG. 6 shown in the upright position.

Referring now to FIGS. 6 and 7, another embodiment of the device in accordance with the present invention is illustrated. For the sake of brevity in the disclosure, only those elements that differ from the first embodiment will be discussed in detail. In addition, like elements will be referred to with like reference numbers, but with the addition of one-hundred to distinguish from the first embodiment. A subhousing 122 is disposed within housing, downstream from the one-way valve. Subhousing 122 has a spherical inner surface 124 with a predetermined inner diameter. The subhousing 122 has an inlet port 126 for receiving fluid from the first region and an outlet port 128 for directing fluid to the second region. The inlet port 126 and the outlet port 128 are disposed approximately diametrically opposite from each other along essentially the same longitudinal axis.

A spherical ball 130 is disposed within subhousing 122. Spherical ball 130 has a ferromagnetic weight 132 disposed off center therein. The remainder of spherical ball may be made of a light-weight material, such as, for example, a biocompatible plastic. Ball 130 has a predetermined outer diameter that is less than the inner diameter of the subhousing 122. Spherical ball 130 has a recess 134 extending about the circumference of the ball. In addition, spherical ball 130 has a through bore 140 extending through the ball 130. Bore 140 is approximately normal to the plane defined by circumferential recess 134.

A first magnetic band 136 surrounds subhousing 112. The first magnetic band 136 has a plane of symmetry that is approximately normal to a line extending between the inlet port 126 and said outlet port 128. A second magnetic band 138 is disposed about outlet port 128. The second magnetic band 138 also has a plane of symmetry that is approximately normal to the line extending between the inlet port 126 and said outlet port 128. The first magnetic band 136 has one charge and the magnetic weight 132 has an opposite charge so that, in one position as illustrated in FIG. 6, they are magnetically attracted toward one another. The second magnetic band 138 has the same charge as the first magnetic band so that, in a second position illustrated in FIG. 7, second magnetic band 138 and magnetic weight 132 are magnetically attracted toward one another.

In use, when the patient is in the supine position, subhousing 122 is placed essentially in a first position which causes the magnetic weight in the spherical ball to align with the first magnetic band such that the circumferential recess 134 within ball 130 is approximately co-linear with respect to the line between the inlet port 126 and the outlet port 128. Thus, the maximum amount of fluid can flow through subhousing 122.

When the patient is in the upright position, subhousing 122 is placed essentially in a second position which causes the magnetic weight in the spherical ball to align with the second magnetic band 138 such that the circumferential recess 134 within ball 130 is normal with respect to the line between the inlet port 126 and the outlet port 128. The first position is disposed approximately ninety degrees from the second position.

Figure 8:
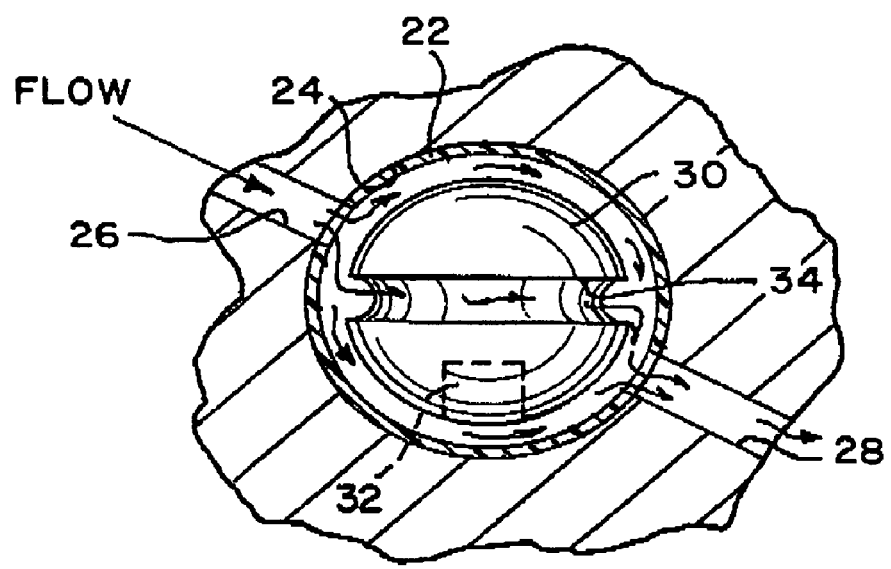
FIG. 8 is a cross-sectional view of the device of FIG. 6, but showing the device without the magnetic bands and in another position.

If magnetic bands 136, 138 are not used, as illustrated in FIG. 8, weight 132 will always be drawn, by the force of gravity, to the lowest possible position within subhousing 122. Thus, as the patient moves from the supine position to the vertical position, the recess 134 will move gradually between the two extreme positions. Thus, the flow rate through the anti-siphon device will gradually reduce from the maximum flow rate (as shown if FIG. 6) to the minimum flow rate (as shown in FIG. 7).

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. An anti-siphon device for limiting the flow of a fluid from a first region of a patient's body to a second region, comprising:
    a housing having a spherical inner surface with a predetermined inner diameter, said housing having an inlet port for receiving fluid from the first region and an outlet port for directing fluid to the second region, said inlet port and said outlet port are disposed approximately diametrically opposite from each other; and
    a spherical ball disposed within said housing, said spherical ball having a ferromagnetic weight disposed off center therein, said spherical ball having an outer diameter that is less than the inner diameter of said housing so that said spherical ball is free to rotate within said housing and the fluid is free to flow between said inner surface of said housing and an outer surface of said spherical ball, said spherical ball having a recess extending about the circumference of said spherical ball.

2. The anti-siphon device according to claim 1, further comprising
    a first magnetic band surrounding said housing, said first magnetic band having a plane of symmetry that is approximately normal to a line extending between said inlet port and said outlet port;
    a second magnetic band disposed about said outlet port, said second magnetic band having a plane of symmetry that is approximately normal to said line.

3. The anti-siphon device according to claim 2, wherein the first magnetic band has one charge and the magnetic weight has an opposite charge.

4. The anti-siphon device according to claim 3, wherein the second magnetic band has the same charge as the first magnetic band.

5. The anti-siphon device according to claim 4, wherein the housing is made of a material that reduces electromagnetic interference.

6. The anti-siphon device according to claim 5, wherein the housing is made of metal.

7. The anti-siphon device according to claim 2, wherein the housing is made of a rigid material that reduces electromagnetic interference.

8. The anti-siphon device according to claim 2, wherein placing the housing in a first position causes the magnetic weight in the spherical ball to align with the first magnetic band such that said circumferential recess defines a plane and said line lies approximately within said plane.

9. The anti-siphon device according to claim 8, wherein placing the housing in a second position causes the magnetic weight in the spherical ball to align with the second magnetic band such that said plane defined by said circumferential recess is normal with respect to said line.

10. The anti-siphon device according to claim 9, wherein the first position is disposed approximately ninety degrees from said second position.

11. The anti-siphon device according to claim 1, wherein the housing is made of a rigid material that reduces electromagnetic interference.

12. The anti-siphon device according to claim 11, wherein the housing is made of metal.

13. The anti-siphon device according to claim 1, wherein said spherical ball has a through bore extending therethrough.

14. The anti-siphon device according to claim 13, wherein said through bore is approximately normal to a plane defined by said circumferential recess.

15. A system for limiting the flow of a fluid from a first region of a patient's body to a second region, comprising:
    a housing having an inlet for receiving fluid from the first region and an outlet for directing fluid to the second region;
    one-way valve disposed within said housing;
    a subhousing disposed within said housing and downstream from said one-way valve, said subhousing having a spherical inner surface with a predetermined inner diameter, said subhousing having an inlet port and an outlet port, said inlet port and said outlet port are disposed approximately diametrically opposite from each other; and
    a spherical ball disposed within said subhousing, said spherical ball having a ferromagnetic weight disposed off center therein, said spherical ball having an outer diameter that is less than the inner diameter of said subhousing so that said spherical ball is free to rotate within said subhousing and the fluid is free to flow between said inner surface of said subhousing and an outer surface of said spherical ball, said spherical ball having a recess extending about the circumference of said spherical ball.

16. The system according to claim 15, further comprising,
a first magnetic band surrounding said subhousing, said first magnetic band having a plane of symmetry that is approximately normal to a line extending between said inlet port and said outlet port;
a second magnetic band disposed about said outlet port, said second magnetic band having a plane of symmetry that is approximately normal to said line.

17. The system according to claim 16, wherein the first magnetic band has one charge and the magnetic weight has an opposite charge.

18. The system according to claim 17, wherein the second magnetic band has the same charge as the first magnetic band.

19. The system according to claim 18, wherein the subhousing is made of a material that reduces electromagnetic interference.

20. The system according to claim 19, wherein the subhousing is made of metal.

21. The system according to claim 16, wherein the subhousing is made of a material that reduces electromagnetic interference.

22. The system according to claim 16, wherein placing the subhousing in a first position causes the magnetic weight in the spherical ball to align with the first magnetic band such that said circumferential recess defines a plane and said line lies approximately within said plane.

23. The system according to claim 22, wherein placing the subhousing in a second position causes the magnetic weight in the spherical ball to align with the second magnetic band such that said plane defined by said circumferential recess is normal with respect to said line.

24. The system according to claim 23, wherein the first position is disposed approximately ninety degrees from said second position.

25. The system according to claim 16, wherein a spring bias of said one-way valve is programmable.

26. The system according to claim 15, wherein the subhousing is made of a material that reduces electromagnetic interference.

27. The system according to claim 26, wherein the subhousing is made of metal.

28. The system according to claim 15, wherein a spring bias of said one-way valve is programmable.

29. The system according to claim 15, wherein said spherical ball has a through bore extending therethrough.

30. The anti-siphon device according to claim 29, wherein said through bore is approximately normal to a plane defined by said circumferential recess.

* * * * *